(12) United States Patent
Kramm et al.

(10) Patent No.: US 7,657,323 B2
(45) Date of Patent: Feb. 2, 2010

(54) ENDOVENOUS DEVICE FOR DISPERSING A DILATING AGENT

(75) Inventors: Berthold Kramm, Aachen (DE); Volker Dörnberger, Tübingen (DE)

(73) Assignee: Medtronic, Inc., Minneapolis, MN (US)

( * ) Notice: Subject to any disclaimer, the term of this patent is extended or adjusted under 35 U.S.C. 154(b) by 98 days.

(21) Appl. No.: 11/189,053

(22) Filed: Jul. 25, 2005

(65) Prior Publication Data

US 2005/0256559 A1 Nov. 17, 2005

Related U.S. Application Data

(62) Division of application No. 10/041,802, filed on Oct. 29, 2001, now Pat. No. 6,936,040.

(51) Int. Cl.
*A61N 1/05* (2006.01)
(52) U.S. Cl. ..................... 607/120; 607/122
(58) Field of Classification Search ................. 607/120, 607/122, 126–128, 116, 119, 121; 600/585
See application file for complete search history.

(56) References Cited

U.S. PATENT DOCUMENTS

| | | | |
|---|---|---|---|
| 4,375,817 A | 3/1983 | Engle et al. | |
| 4,506,680 A * | 3/1985 | Stokes | 607/120 |
| 4,819,662 A * | 4/1989 | Heil et al. | 607/116 |
| 4,946,457 A | 8/1990 | Elliott | |
| 4,955,895 A * | 9/1990 | Sugiyama et al. | 606/194 |
| 5,033,998 A | 7/1991 | Corday et al. | |
| 5,234,407 A * | 8/1993 | Teirstein et al. | 604/528 |
| 5,305,745 A * | 4/1994 | Zacouto | 600/324 |
| 5,451,233 A | 9/1995 | Yock | |
| 5,571,085 A | 11/1996 | Accisano, III | |
| 5,571,161 A * | 11/1996 | Starksen | 607/122 |
| 5,609,629 A * | 3/1997 | Fearnot et al. | 623/1.42 |
| 5,611,775 A * | 3/1997 | Machold et al. | 604/509 |

(Continued)

FOREIGN PATENT DOCUMENTS

EP 0649637 A1 8/1989

(Continued)

OTHER PUBLICATIONS

Prosecution history of parent U.S. Appl. No. 10/041,802 including: Restriction Requirement dated Mar. 9, 2004, Restriction Requirement dated Mar. 24, 2004, Response dated Apr. 8, 2004, Restriction Requirement dated Jun. 22, 2004, Response to Restriction Requirement dated Jul. 22, 2004, Non-Final Office Action dated Nov. 15, 2004, Response dated Feb. 15, 2005, Examiner Interview Summary dated Mar. 9, 2005, Final Office Action dated Mar. 9, 2005, Response dated Apr. 6, 2005, Notice of Allowance dated Apr. 25, 2005.

(Continued)

*Primary Examiner*—Kennedy J Schaetzle
(74) *Attorney, Agent, or Firm*—Stephen W. Bauer

(57) ABSTRACT

Apparatus and methods are disclosed for inserting electrical leads within a heart. A method is provided for positioning a medical electrical lead in a cardiac vein. The method comprises inserting a lead within a coronary sinus, dispersing at least one vasodilating agent to dilate at least one cardiac vein, and inserting the lead into a dilated cardiac vein.

14 Claims, 8 Drawing Sheets

U.S. PATENT DOCUMENTS

| | | | |
|---|---|---|---|
| 5,681,278 A | 10/1997 | Igo et al. | |
| 5,709,874 A * | 1/1998 | Hanson et al. | 424/423 |
| 5,755,766 A * | 5/1998 | Chastain et al. | 607/122 |
| 5,947,977 A * | 9/1999 | Slepian et al. | 606/108 |
| 6,021,340 A * | 2/2000 | Randolph et al. | 600/381 |
| 6,070,104 A * | 5/2000 | Hine et al. | 607/123 |
| 6,156,195 A * | 12/2000 | Nakamura et al. | 210/198.2 |
| 6,355,026 B1 | 3/2002 | Mick | |
| 6,358,247 B1 | 3/2002 | Altman et al. | |
| 6,408,213 B1 | 6/2002 | Bartig et al. | |
| 6,510,348 B2 * | 1/2003 | Clemens et al. | 607/119 |
| 6,584,362 B1 * | 6/2003 | Scheiner et al. | 607/122 |
| 6,711,443 B2 | 3/2004 | Osypka | |
| 6,936,040 B2 | 8/2005 | Kramm et al. | |
| 2002/0082552 A1 * | 6/2002 | Ding et al. | 604/103.02 |
| 2003/0023295 A1 * | 1/2003 | Osypka | 607/122 |
| 2003/0171796 A1 | 9/2003 | Hine et al. | |
| 2005/0177218 A1 | 8/2005 | Kramm et al. | |

FOREIGN PATENT DOCUMENTS

| | | |
|---|---|---|
| EP | 0919254 A2 | 11/1998 |

OTHER PUBLICATIONS

Prosecution history of U.S. Appl. No. 11/099,773 including: Non-Final Office Action dated Jul. 5, 2006, Amendment and Response dated Sep. 25, 2006, Non-Final Office Action dated Nov. 22, 2006.

* cited by examiner

ENDOVENOUS DEVICE FOR DISPERSING A DILATING AGENT

This application is a Divisional of application Ser. No. 10/041,802, filed Oct. 29, 2001, entitled "Method and Apparatus for Endovenous Pacing Lead," now U.S. Pat. No. 6,936,040.

FIELD OF THE INVENTION

This invention relates generally to a method and apparatus for electrically stimulating a heart, and, more particularly, to a method and apparatus for positioning and fixating an electrode lead to stimulate and/or sense activity in the heart.

DESCRIPTION OF THE RELATED ART

Since their earliest inception some forty years ago, there has been a significant advancement in body-implantable electronic medical devices. Today, these implantable devices include therapeutic and diagnostic devices, such as pacemakers, cardioverters, defibrillators, neural stimulators, drug administering devices, among others for alleviating the adverse effects of various health ailments. Today's implantable medical devices are also vastly more sophisticated and complex than their predecessors, and are therefore capable of performing considerably more complex tasks for reducing the effects of these health ailments.

A variety of different implantable medical devices (IMD) are available for therapeutic stimulation of the heart and are well known in the art. For example, implantable cardioverter-defibrillators (ICDs) are used to treat patients suffering from ventricular fibrillation, a chaotic heart rhythm that can quickly result in death if not corrected. In operation, the ICD continuously monitors the electrical activity of a patient's heart, detects ventricular fibrillation, and in response to that detection, delivers appropriate shocks to restore normal heart rhythm. Similarly, an automatic implantable defibrillator (AID) is available for therapeutic stimulation of the heart. In operation, an AID device detects ventricular fibrillation and delivers a non-synchronous high-voltage pulse to the heart through widely spaced electrodes located outside of the heart, thus mimicking transthoratic defibrillation. Yet another example of a prior art cardioverter includes the pacemaker/cardioverter/defibrillator (PCD) disclosed, for example, in U.S. Pat. No. 4,375,817 to Engle, et al. This device detects the onset of tachyarrhythmia and includes means to monitor or detect progression of the tachyarrhythmia so that progressively greater energy levels may be applied to the heart to interrupt a ventricular tachycardia or fibrillation. Numerous other, similar implantable medical devices, for example a programmable pacemaker, are further available.

Regardless of the exact construction and use, each of the above-described IMDs generally comprise three primary components: a low-power control circuit, a high-power output circuit, and a power source. The control circuit monitors and determines various operating characteristics, such as, for example, rate, synchronization, pulse width and output voltage of heart stimulating pulses, as well as diagnostic functions such as monitoring the heart. Conversely, the high-power output circuit generates electrical stimulating pulses to be applied to the heart via one or more leads in response to signals from the control circuit.

The power source "powers" both the low-power control circuit and the high-power output circuit. As a point of reference, the power source is typically required to provide 10-20 microamps to the control circuit and a high power pulse to the output circuit. Depending upon the particular IMD application, the high-power output circuit may require a stimulation energy of as little as 0.1 Joules for pacemakers to as much as 40 Joules for implantable defibrillators. In addition to providing sufficient stimulation energy, the power source must possess a low self-discharge to have a useful life of many years, must be highly reliable, and must be able to supply energy from a minimum packaged volume.

Modern electrical therapeutic and diagnostic devices for the heart require a reliable electrical connection between the device and a particular region of the heart. Typically, a medical electrical "lead" is used for the desired electrical connection. One type of commonly used implantable lead is a transvenous lead. Transvenous leads are positioned through the venous system to attach or electrically connect at their distal end to the heart. At their proximal end, they are typically connected to the electrical therapeutic and diagnostic device, which may be implanted. Such leads normally take the form of a long, generally straight, flexible, insulated conductor. Among the many advantages of transvenous leads is that they permit an electrical contact with the heart without physically exposing the heart itself, i.e., major thoracic surgery is not required.

The specific design of transvenous leads is varied, depending upon the region of the heart to which it is to be connected. For example, U.S. Pat. No. 6,070,104 discloses an implantable lead capable of stimulating and/or sensing multiple chambers of the heart. Multiple electrodes are located on the lead and spaced apart so that multiple chambers may be separately stimulated and/or sensed. The structure and size of patients' hearts varies considerably. Accordingly, the optimal locations for positioning the electrodes within a vein may vary substantially, depending on the anatomy of the patient.

The left ventricle is a portion of the heart that can be difficult in which to locate a lead due to the specific anatomical structure of the heart. One type of implantable lead that is used for positioning adjacent to the left ventricle is an endovenous epicardial lead. A typical left ventricular endovenous epicardial lead is one that is initially routed in the typical manner into the right atrium of the heart. From the right atrium the lead is guided through the coronary sinus and into a cardiac vein that is attached to the left side of the heart. The lead is then inserted into the cardiac vein and extended in an attempt to reach a desired distal location adjacent to the left ventricle of the heart. This procedure is difficult due to the tortuous path that the lead is subjected to and due to the reduced diameter of the cardiac veins in the more distal locations. Another factor that complicates the left ventricular procedure is that the leads are limited in active fixation mechanisms. Right ventricular leads can utilize fixation mechanisms such as tines and screw-in lead tips. These fixation methods may be difficult for use with left ventricular leads due to the specific anatomical structure of the left sided endovenous system.

There is a need for improved methods and apparatus for more efficient placement and fixation of endovenous epicardial left ventricular pacing leads within a heart.

SUMMARY OF THE INVENTION

In one aspect of the present invention, an apparatus is provided for positioning a medical electrical lead in a heart. The medical electrical lead comprises an electrode coupled adjacent a distal end portion of the medical electrical lead, the distal end portion of the lead capable of insertion into the coronary sinus of a patient. A distribution device is attached to the distal end of the lead and adapted for dissipation of a material into the coronary sinus and into a cardiac vein. The material can comprise a vasodilating agent.

In another embodiment of the invention a medical catheter device comprising a flexible tubular body having a distal end and a proximal end is disclosed. A first lumen is disposed within the flexible tubular body and is capable of transporting an electrical lead through the first lumen and out the distal end of the flexible tubular body. There is also a distribution device capable of emitting a vasodilating agent adjacent the distal end of the flexible tubular body.

In yet another aspect of the present invention, a method for positioning a medical electrical lead in a cardiac vein is disclosed. The method comprises inserting a lead within a portion of a patient's body, dispersing at least one vasodilating agent to dilate at least one vessel, and inserting the lead into a dilated vessel.

BRIEF DESCRIPTION OF THE DRAWINGS

The invention may be understood by reference to the following description taken in conjunction with the accompanying drawings, in which like reference numerals identify like elements, and in which.

Figure 1:
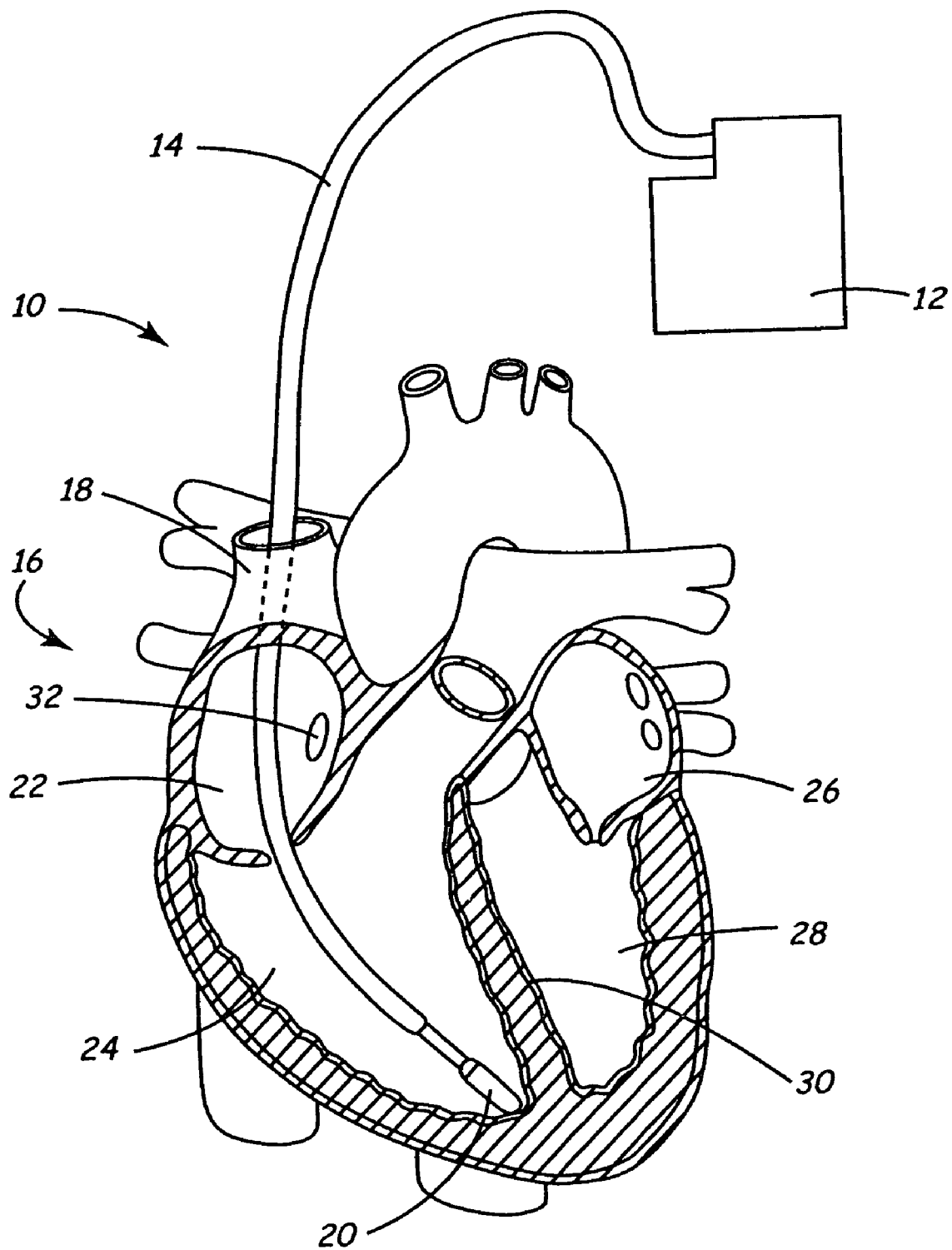
FIG. 1 schematically illustrates a prior art embodiment of an implanted medical device with an associated lead positioned within the right ventricle of a heart.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Embodiments of the present invention concern an electrical lead that may be implanted and used to stimulate and/or sense the atrium and ventricle of the left side of the heart through the coronary sinus. As is well known, there has to date been a great difficulty in reliably implanting leads within the coronary sinus and cardiac veins. For example, a typical coronary sinus is 10 millimeters at its largest diameter (near the outflow to the right atrium) and narrows until it has a diameter of between approximately 2-3 millimeters and merges to the great cardiac vein. Thus any leads having larger sizes could be expected to diminish the flow of blood through the coronary sinus. The fixation of a lead within the coronary sinus or cardiac vein is further complicated by the fact that, unlike a heart chamber where the fibrotic tissue response is used to assist lead fixation, no such fibrotic response can be expected in the vein. As such no fibrotic tissue response is available to assist in lead fixation. Thus, embodiments of the present invention comprise a lead implantation apparatus and method that includes the dispensing of a vasodilating agent that induces a temporary dilating of the venous vessels during positioning of the lead. The vasodilating agent generally relaxes the cardiac vein, thereby making it easier to insert the cardiac lead into more distal locations. Once the effects of the vasodilating agent has ceased, the cardiac vein will contract to its original size, thus fixating the cardiac lead by the contraction produced by the vascular musculature. This fixation can enable an increased lead stability and thereby an increased performance of the lead.

FIG. 1 illustrates a prior art implantable medical device (IMD) system 10, which includes an implantable electronic device 12, such as a pacemaker, defibrillator, or the like, that has been implanted in a patient. The device 12 is housed within a hermetically sealed, biologically inert outer canister or housing, which may itself be conductive so as to serve as an electrode in the pacemaker's pacing/sensing circuit. One or more pacemaker leads, collectively identified with reference numeral 14 in FIG. 1 are electrically coupled to the pacemaker 12 in a conventional manner and extend into the patient's heart 16 via a vein, typically the superior vena cava vein 18.

Disposed generally near a distal end 20 of the leads 14 are one or more exposed conductive electrodes for sensing cardiac activity, delivering electrical pacing stimuli to the heart 16, or providing a stimulating voltage to defibrillate the heart 16. The leads 14 may be implanted with their distal end situated adjacent the right atrium 22 or the right ventricle 24, or both, of the heart 16. The illustration of FIG. 1 shows the distal end 20 of the lead 14 disposed within the right ventricle 24 of the heart 16. Due to the anatomical structure of the heart 16, it is more difficult to position a lead 14 within or adjacent to the left atrium 26 or left ventricle 28. The septum 30 is a wall that separates the right cavities 22, 24 from the left cavities 26, 28 of the heart 16 and prevents direct fluid communication between them. The septum 30 likewise presents a barrier to direct insertion of the lead 14 into either of the left cavities 26, 28 using the typical pathway of the superior vena cava 18. An alternate path to a location adjacent the left cavities 26, 28 is through the coronary sinus 32 that provides a passageway for oxygen depleted blood from the left side of the heart 16 to enter the right atrium 22.

Figure 2:
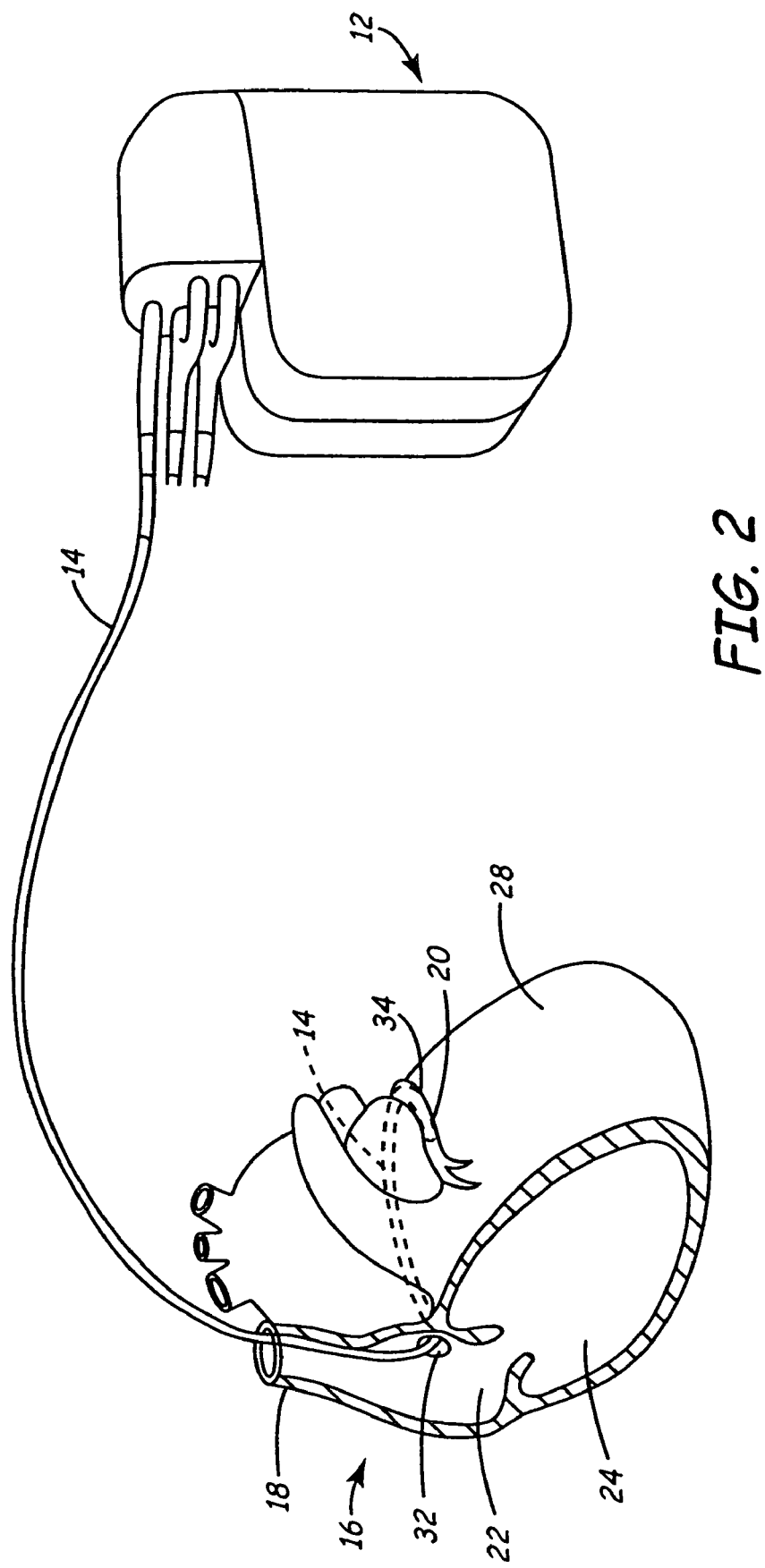
FIG. 2 schematically illustrates a prior art embodiment of an implanted medical device with an endovenous epicardial lead positioned adjacent the left ventricle of a heart.

FIG. 2 schematically illustrates a prior art embodiment of an implanted medical device with an endovenous epicardial lead 14 passing through the superior vena cava 18, through the right atrium 22, entering the coronary sinus 32 and its distal end 20 positioned within a cardiac vein 34 adjacent to the left ventricle 28 of a heart 16. The ability to position a lead 14 within this section of the heart 16 enables the implantable medical device (IMD) system 10 to provide left ventricle 28 and atrial 26 pacing, coronary sinus 32 defibrillation, left ventricle 28 defibrillation, other delivery of therapy and/or other form of sensing.

As discussed above, the placement of a lead 14 within the coronary sinus 32 and into a cardiac vein 34 may be problematic due to the physical restrictions and the difficulty in fixating the distal end 20 of the lead 14. The various embodiments of the present invention address these issues and are described herein. To the extent that certain components and procedures referenced herein are conventional in their design and operation, such components/procedures will not be described herein in detail, as it is believed that design and implementation of such components and the performance of such methods would be a matter of routine practice to those of ordinary skill in the art. For example, various processes for passing a catheter lead through the tortuous path of a representative cardiac venous system is well known in the art.

Figure 3:
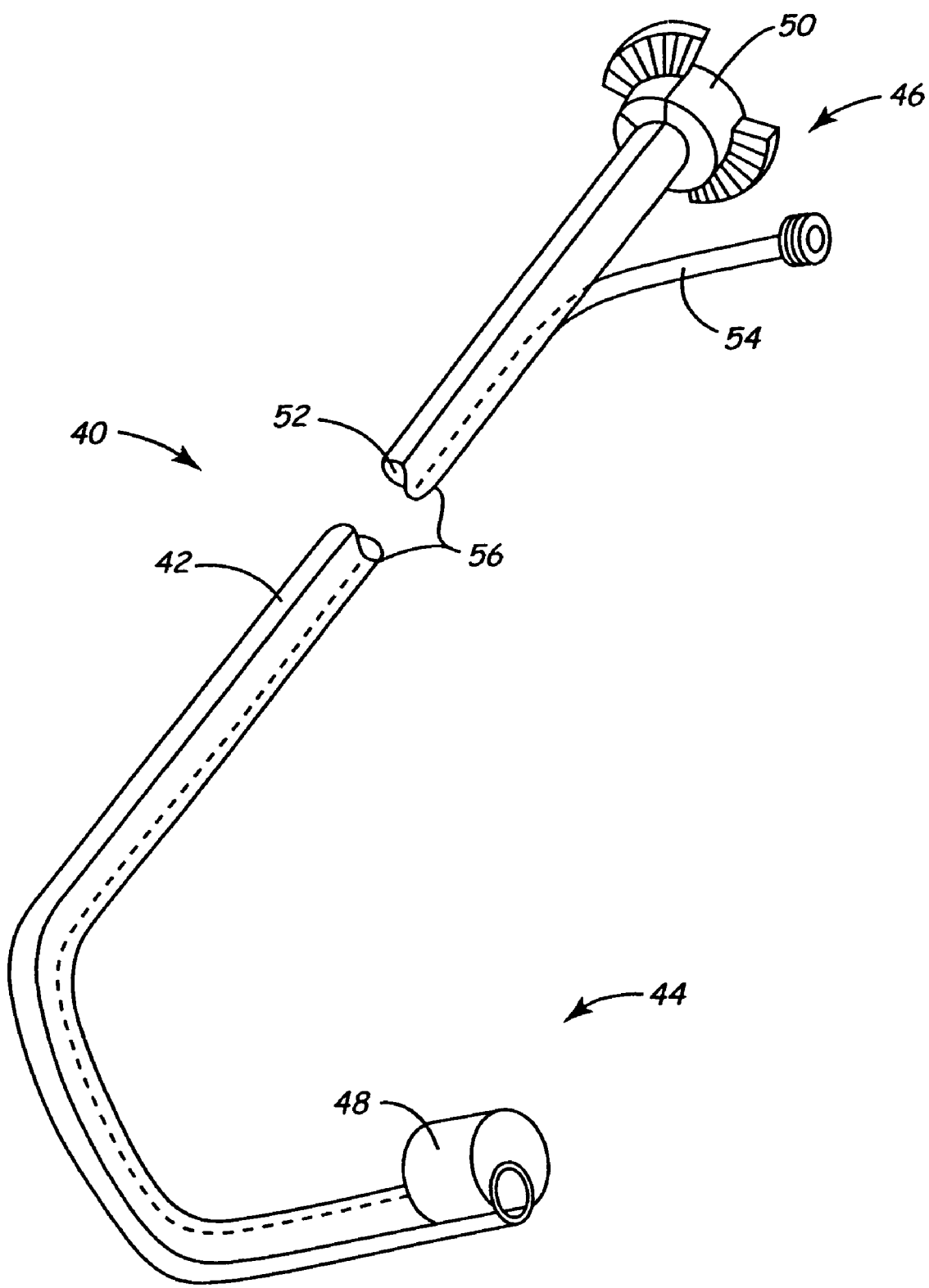
FIG. 3 is a perspective view of a guide catheter constructed in accordance with the principles of the present invention.

Referring now to FIG. 3, an exemplary guide catheter 40 includes a flexible tubular body 42 having a distal end 44 and a proximal end 46. A distributor 48 is mounted on the distal end 44 of the flexible tubular body 42, and a hub 50 is mounted on the proximal end 46 of the flexible tubular body 42. The axial lumen 52 of the tubular body 42 provides a passageway for a lead (e.g., an electrical lead) to be directed out of the distal end 44 of the catheter 40. A secondary connector 54 is connected to the tubular body 42 and to a secondary passageway or lumen 56 that is connected to the distributor 48. The secondary connector 54, second lumen 56, and the distributor 48 provide a means for transporting a material from the proximal end 46 to the distal end 44 of the catheter 40. The distributor 48 provides a means of dispersing the material within a vessel, such as a coronary sinus and/or a cardiac vein. The material can comprise a vasodilating agent that promotes the dilation of the one or more vessels which the vasodilating agent contacts. Examples of vasodilating agents that can be used include Papaverin and Moxaverin.

The dispensing of the vasodilating agent induces a temporary dilating of the venous vessels, relaxing the cardiac veins, thereby making it easier to place a cardiac lead through the axial lumen 52 of the catheter 40 and into more distal locations in the vessel, such as a cardiac vein. After placement of the lead within the vessel, the catheter 40 can be removed, while leaving the lead implanted within the vessel. Once the effects of the vasodilating agent has ceased, the vessel will generally contract to its original size, thus assisting the fixation of the lead within the vessel. Thus the vasodilating agent can assist in the placement of the lead into more distal locations within the heart and can assist in the fixation of the lead within the vessel once placed. This fixation can provide increased lead stability and thereby an increased performance of the lead. It is possible that the secondary connector 54 can connect directly to the axial lumen 52 rather than a separate passageway 56 as shown. Vasodilating agents can be injected through the secondary connector 54, through the axial lumen 52 and to the distal end 44 of the catheter 40 for distribution either through the distributor 48 or out the end of the catheter 40.

Figure 4:
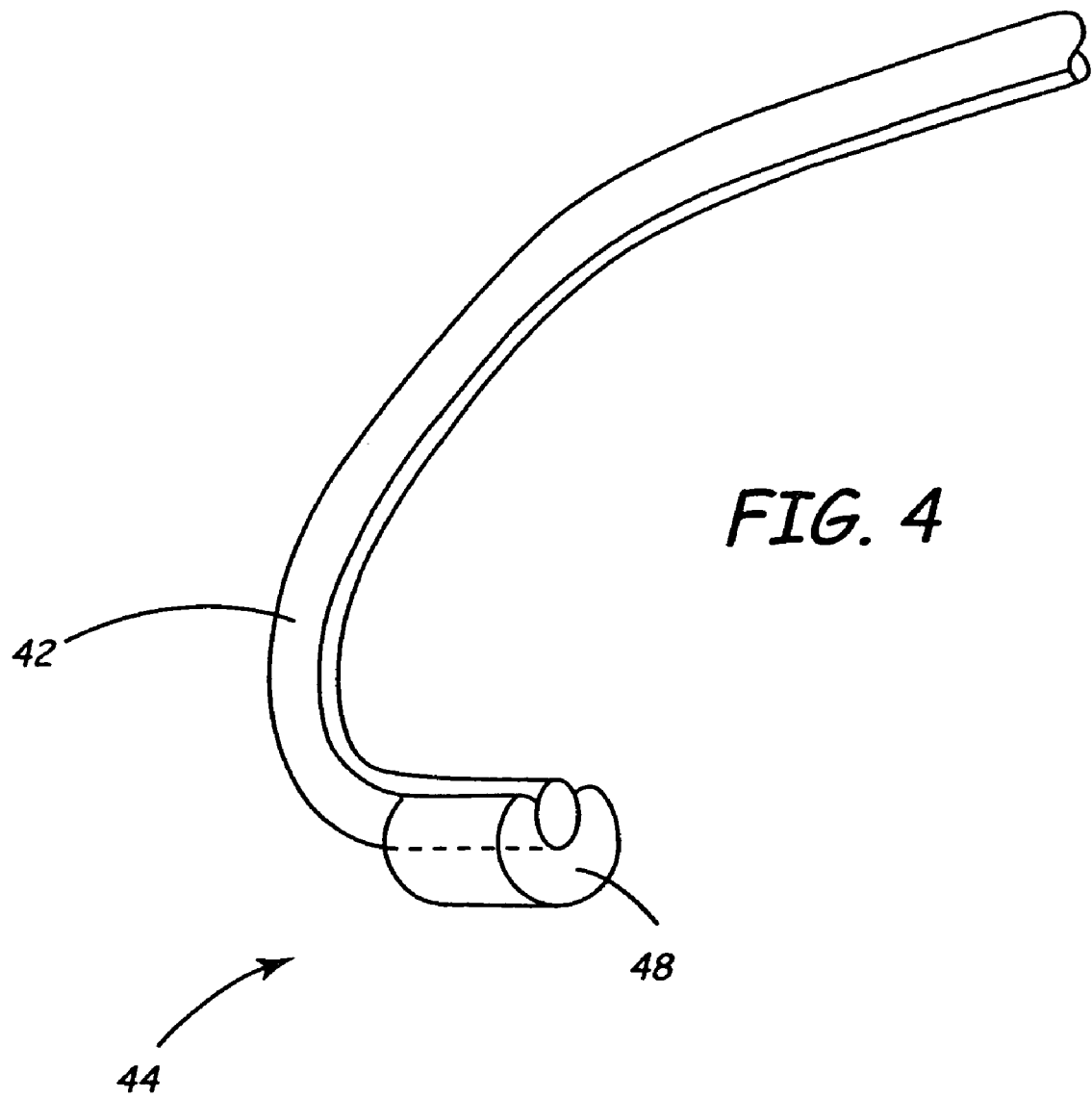
FIG. 4 illustrates an alternative distal end of the guide catheter of FIG. 3, designed specifically for introduction to the coronary sinus.

FIG. 4 illustrates an alternate distal end 44 of the tubular body 42 of the catheter 40 embodiment shown in FIG. 3. This illustration is configured for introduction of the distal end 44 of the tubular body 42 into the coronary sinus.

Figure 5A:
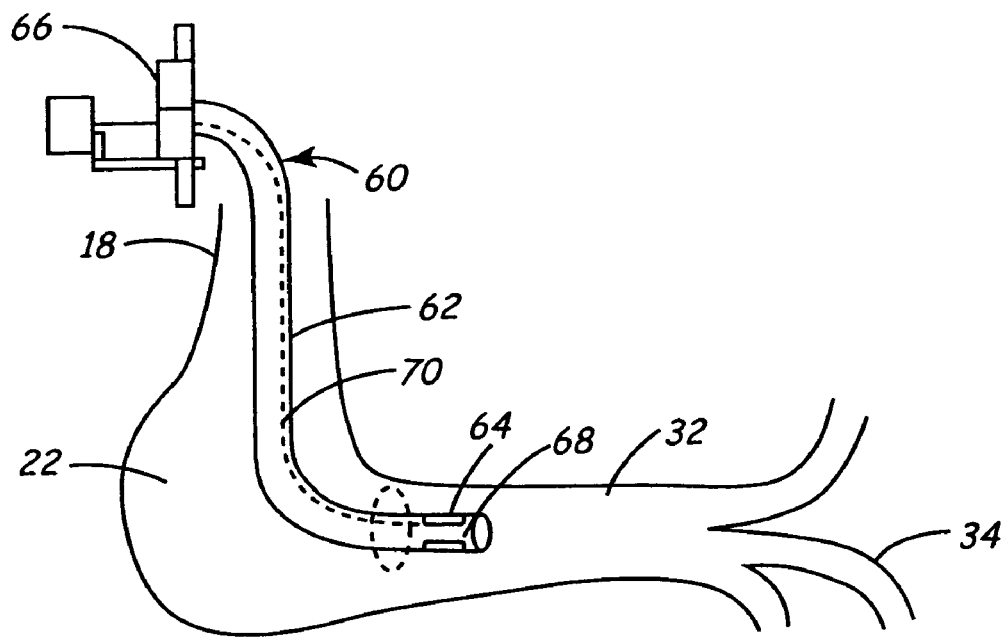
FIG. 5A schematically illustrates an alternate embodiment guide catheter constructed in accordance with the principles of the present invention.

Referring to FIG. 5A, an exemplary guide catheter 60 is shown inserted into the superior vena cava 18, passing through the right atrium 22 and passing into the coronary sinus 32. The guide catheter 60 comprises a flexible tubular body 62 having a distal end 64 and a proximal end 66. At the distal end 64 of the tubular body 62 is a distributor 68, which is shown within the guide catheter 60. An alternate passageway 70 provides a path from the proximal end 66 of the catheter 60 to the distributor 68 at the distal end 64 of the tubular body 62.

Figure 5B:
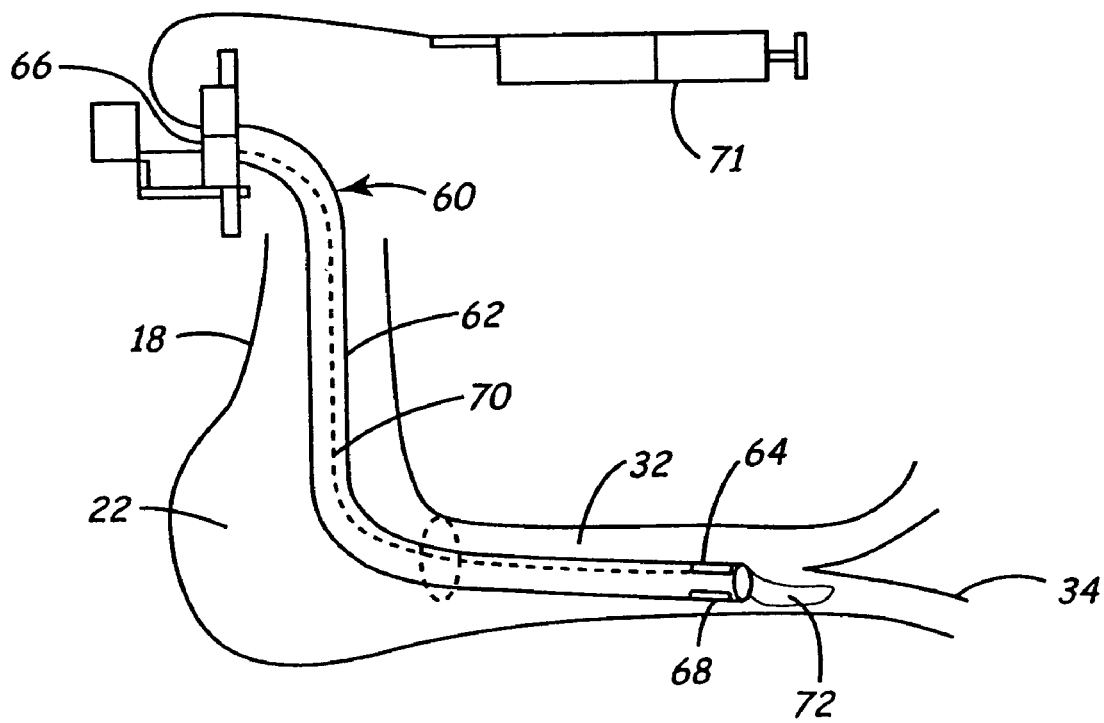
FIG. 5B schematically illustrates the alternate embodiment guide catheter shown in FIG. 5A dispersing vasodilating agents into a cardiac vein in accordance with the principles of the present invention.

FIG. 5B shows the guide catheter 60 inserted through the coronary sinus 32 to the cardiac veins 34. A vasodilating agent 72 is shown dispensed from the distributor 68 at the distal end 64 of the catheter 60. In response to pressure applied by an injector element 71, the vasodilating agent 72 is forced through the alternate passageway 70 and is dispersed from the distributor 68 into one or more of the cardiac veins 34, promoting dilation of the cardiac veins 34. Upon the dilation of the cardiac veins 34 it may be possible to insert the guide catheter 60 further into one of the cardiac veins 34, where a lead can be disposed into a more distal location within the cardiac vein than would be possible without the dilating effects promoted by the vasodilating agent 72. An alternate procedure entails the dispensing of the vasodilating agent 72 out the distal end 64 of the catheter 60, followed by the insertion of an electrical lead (not shown) through the catheter 60, out the distal end 64 and into one of the cardiac veins 34 that are dilated from the effects of the vasodilating agent 72.

Figure 6:
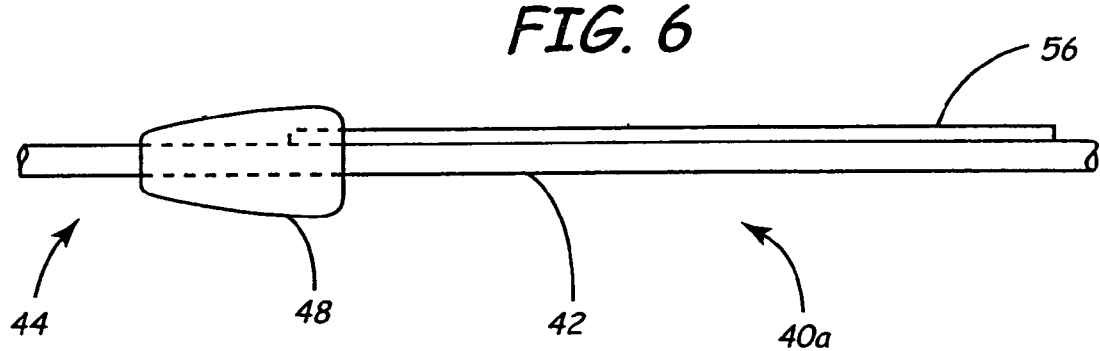
FIG. 6 schematically illustrates an alternate embodiment guide catheter constructed in accordance with the principles of the present invention.

FIG. 6 presents an alternate embodiment of a catheter device 40a having a flexible tubular body 42 and a distribution device 48 located approximate the distal end 44 of the device 40a. A secondary passageway 56 connects to the distribution device 48 and enables vasodilating agents to be transported to the distribution device 48. The distribution device 48 may comprise a porous material that dissipates the vasodilating agents in a substantially controlled manner. The distribution device 48 can typically dispense the vasodilating agents in a more uniform pattern than dispensing without the use of a distribution device 48.

Figure 7:
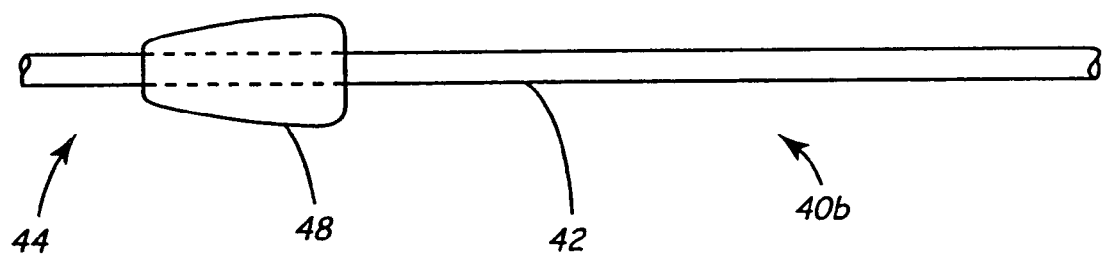
FIG. 7 schematically illustrates an alternate embodiment guide catheter constructed in accordance with the principles of the present invention.

FIG. 7 presents an alternate embodiment of a catheter device 40b having a flexible tubular body 42 and a distribution device 48 located approximate the distal end 44 of the device 40b. In this particular embodiment there is no separate passageway for transmitting the vasodilating agents to the distribution device 48. The distribution device 48 can be impregnated with the vasodilating agents prior to the catheter device 40b being inserted into the patient. The design parameters of the distribution device 48 material, such as porosity of the material and the relative surface tensions of the distribution device 48 material and the vasodilating agents, will determine the rate of dissipation of the vasodilating agents from the distribution device 48. The distribution device 48 can comprise a sponge-like substance that can be saturated or impregnated by the vasodilating agents. Vasodilators can also be applied by chemically binding to or modifying the distribution device 48 material.

Cardiac pacing leads can also be inserted and placed within a patient without the use of a catheter device. In these cases the vasodilator agents can be applied through the cardiac pacing lead itself. Cardiac pacing leads can comprise an elongated flexible body. The body of the lead can have a tubular shape and can be constructed of polyurethane or other similar material used within the medical industry for use inside the human body. The lead can comprise a core of electrically conductive material that is surrounded by a layer of insulative material. The lead will typically include an electrode that is coupled to or adjacent to the distal end of the lead. The lead can include an expandable helical coil coupled to its distal end.

Figure 8:
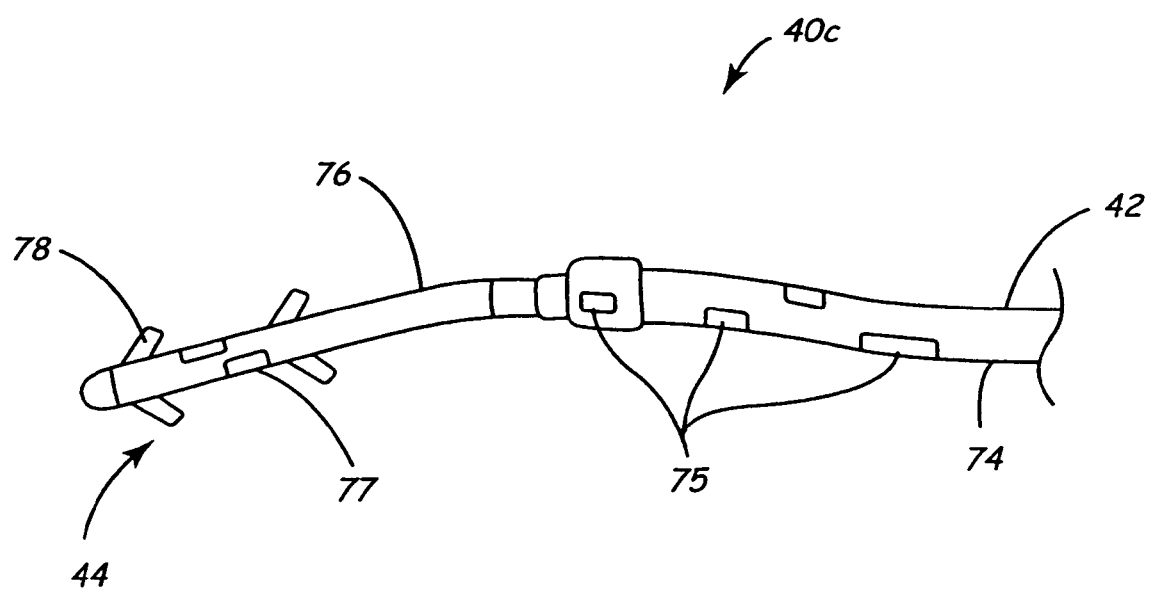
FIG. 8 schematically illustrates an alternate embodiment guide catheter constructed in accordance with the principles of the present invention.

FIG. 8 presents an alternate embodiment of the invention comprising an electrical lead device 40c having an elongated flexible tubular body 42 and a distal end 44. In this particular embodiment the tubular body 42 comprises a first section 74 and a more distal second section 76 that has a smaller diameter than the first section 74. The lead 40c can be tapered along a longitudinal axis of the elongated flexible body 42. The tapered shape can assist in the placement of the lead 40c to more distal locations within a vessel, such as a cardiac vein. The first section 74 has distribution apertures 75 and the second section 76 has distribution apertures 77, both capable of dispersing a vasodilating agent. There can be separate passageways to each of the first and second section apertures 75, 77, which enable the dispersion of different quantities of vasodilating agents from each.

The reduced diameter of the second section 74 can enable the insertion of the electrical lead device 40c into more distal locations within the patient. The particular embodiment shows protrusions 78 from the distal end 44 of the lead 40c. The protrusions 78 can assist in providing electrical contact between the lead 40c and the cardiac vein and can assist in the fixation mechanism of the lead 40c to the heart. Anchoring means attached to the distal end 44 of the lead 40c can assist the fixation of the lead within a cardiac vein. Examples of anchoring means include projections, expanding helical coils and ribs on the exterior surface of the lead. These can all assist with the contraction of the vein in providing a fixation of the lead within the cardiac vein.

In some cases a guide wire is used to initiate the insertion into a particular location within the heart, such as a cardiac vein. The guide wire can be used in conjunction with the lead, such as having the guide wire proceed through a axial lumen within the lead, whereby after the placement of the lead the guide wire can be removed from the lumen, leaving the lead implanted within the patient. These leads are commonly referred to as an "over-the-wire" type of implantable electrical lead.

Figure 9:
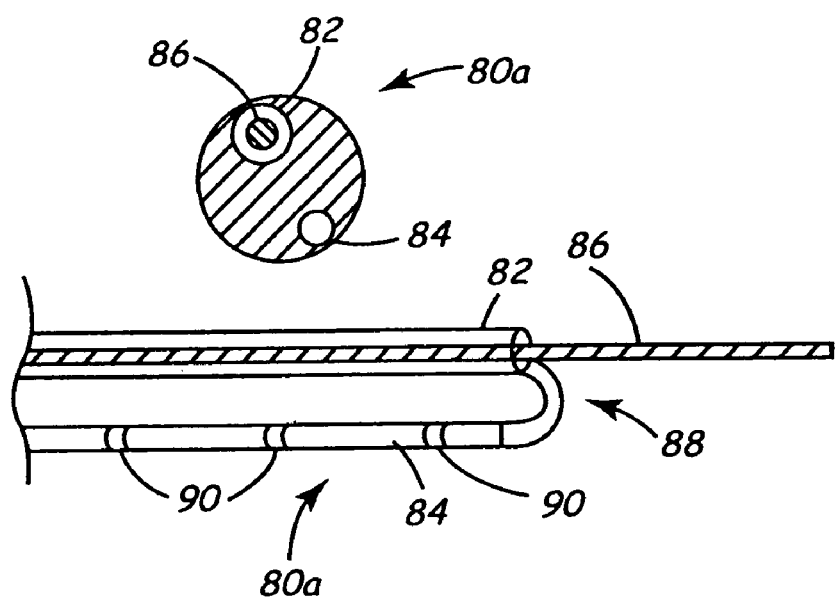
FIG. 9 shows cross-sectional views of one embodiment of the invention.

FIG. 9 shows cross-sectional views of one embodiment of the invention comprising a pacing lead 80a having a first lumen 82 and a second lumen 84. The first lumen 82 is used to house a guide wire 86 while the second lumen 84 provides a passageway to the distal end 88 of the lead 80a. The second lumen 84 can be used to transport and dispense vasodilating agents to the distal end 88 of the lead 80 and can comprise a plurality of outlets 90 to dissipate the vasodilating agents.

Figure 10:
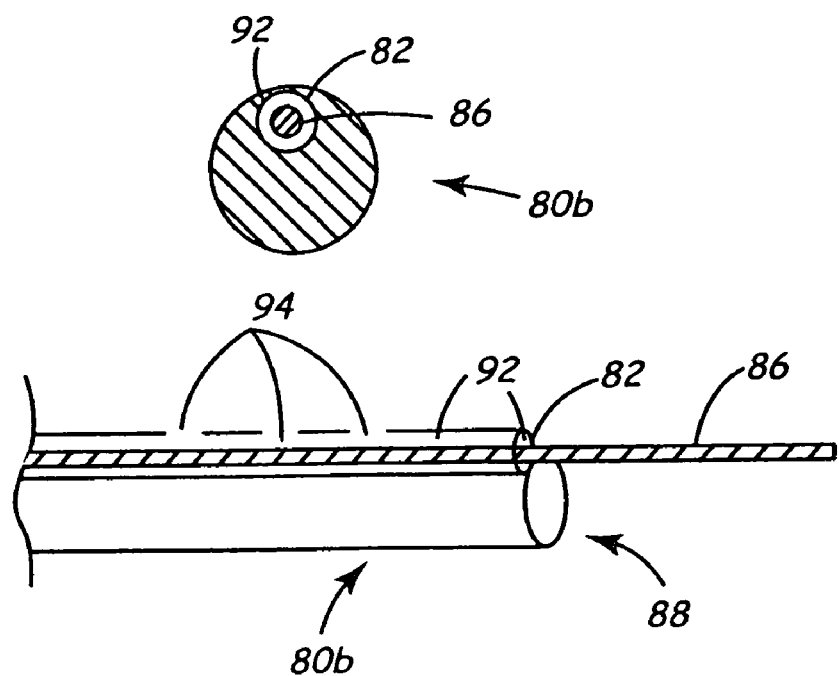
FIG. 10 illustrates cross-sectional views of one particular embodiment of the invention.

FIG. 10 illustrates cross-sectional views of one particular embodiment of the invention in which the vasodilating agents are transferred to the distal end of the lead through the annulus area between the guide wire and the lumen within the lead. The embodiment of FIG. 10 comprises a pacing lead 80b having a first lumen 82 used to house a guide wire 86. An annulus area 92 between the first lumen 82 and the guide wire 86 can be used to transport and dispense vasodilating agents to the distal end 88 of the lead 80b and can comprise a plurality of outlets 94 along the length of the lead 80 to dissipate the vasodilating agents. As with the embodiments of catheter devices, such as shown in FIG. 6, the embodiment of the lead 80 shown in FIG. 10 can further comprise a means of distribution to more evenly dissipate the vasodilating agent (e.g. a distribution device 48).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below.

The invention claimed is:

1. A medical electrical lead device, comprising:
an elongated flexible lead body having a distal end portion and a proximal end portion, the lead body being adapted for insertion through a superior vena cava of a patient and passage through a coronary sinus of a patient to position the distal end within a cardiac vein adjacent to a left ventricle of a patient;
an electrode coupled to the distal end of the lead body;
means coupled to the distal end of the lead body for anchoring the electrode within the cardiac vein; and
means formed at the distal end portion of the lead body proximal to the electrode for dispersing a vasodilating agent within a vessel during insertion and passage of the lead body to position the distal end within the cardiac vein, wherein the vasodilating agent is delivered along the lead body to the means for dispersing from the proximal end, and wherein the means for dispersing includes a plurality of apertures formed in the lead body to disperse the vasodilating agent.

2. A medical electrical lead device as set forth in claim 1, wherein the lead is an over-the-wire lead.

3. A medical electrical lead device, as set forth in claim 1, wherein the elongated flexible body comprises a flexible tube, and the apertures are formed in the flexible tube.

4. A medical electrical lead device, as set forth in claim 1, wherein the elongated flexible body comprises a tube constructed with material selected from the group consisting of polyurethane and silicone.

5. A medical electrical lead device, as set forth in claim 1, wherein said lead is tapered along a longitudinal axis of the elongated flexible body.

6. A medical electrical lead device, as set forth in claim 1, wherein the lead comprises a core of electrically conductive material surrounded by a layer of insulative material.

7. A medical electrical lead device as set forth in claim 1, wherein the anchoring means comprises an expandable helical coil coupled to its distal end.

8. The medical electrical lead device of claim 1, further comprising a fluid source containing the vasodilating agent, wherein the source is coupled to provide the vasodilating agent to the dispersing means.

9. The medical electrical lead device of claim 1, further comprising:
a first lumen to accommodate a guide wire; and a second lumen that receives the vasodilating agent at the proximal end of the second lumen and delivers the vasodilating agent along the lead body to the means for dispersing, wherein the second lumen defines the plurality of apertures.

10. The medical electrical lead device of claim 1, further comprising a lumen to accommodate a guide wire, receive the vasodilating agent at the proximal end of the lumen, and deliver the vasodilating agent along the lead body to the means for dispersing in an annulus area between the guide wire and the lumen, wherein the lumen defines the plurality of apertures.

11. The medical electrical lead device of claim 1, wherein the plurality of apertures are formed at different positions along a length of the elongated flexible lead body, and some of the apertures are configured to disperse different quantities of the vasodilating agent.

12. A medical catheter device, comprising:
- a flexible tubular body having a distal end and a proximal end;
- a first lumen disposed within the flexible tubular body capable of transporting an electrical lead through the first lumen and out the distal end of the flexible tubular body to an implant site within a cardiac vein adjacent to a left ventricle of a patient;
- means for dispersing a vasodilating agent within a vessel during insertion and passage of the tubular body to position the distal end within the cardiac vein, wherein the means for dispersing a vasodilating agent is attached near the distal end of the tubular body and comprises a sponge-like material, wherein the vasodilating agent is selectively delivered from the proximal end to the means for dispersing; and
- a fluid source containing the vasodilating agent, wherein the source is coupled to provide the vasodilating agent to the dispersing means.

13. The medical catheter device of claim 12, wherein the sponge-like material is capable of being saturated or impregnated with the vasodilating agent.

14. A medical catheter device, comprising:
- a flexible tubular body having a distal end and a proximal end;
- a first lumen disposed within the flexible tubular body capable of transporting an electrical lead through the first lumen and out the distal end of the flexible tubular body to an implant site within a cardiac vein adjacent to a left ventricle of a patient;
- means for dispersing a vasodilating agent within a vessel during insertion and passage of the tubular body to position the distal end within the cardiac vein, wherein the means for dispersing a vasodilating agent is attached near the distal end of the tubular body and the vasodilating agent is selectively delivered from the proximal end to the means for dispersing;
- a second lumen for transporting the vasodilating agent from the proximal end to the distal end of the tubular body; and
- a fluid source containing the vasodilating agent, wherein the source is coupled to provide the vasodilating agent to the second lumen.

* * * * *